United States Patent [19]

Chen et al.

[11] Patent Number: 5,756,536
[45] Date of Patent: May 26, 1998

[54] MICROBIAL TRANSFORMATION OF TAXOL AND CEPHALOMANNINE

[75] Inventors: Shieh-Shung Tom Chen, Morganville, N.J.; Ching-jer Chang, West Lafayette, Ind.

[73] Assignee: Purdue Research Foundation, West Lafayette, Ind.

[21] Appl. No.: 730,837

[22] Filed: Oct. 17, 1996

Related U.S. Application Data

[60] Provisional application No. 60/006,241 Nov. 3, 1995.
[51] Int. Cl.⁶ .................... A61K 31/335; C07D 305/14
[52] U.S. Cl. .................... 514/449; 549/510; 549/511
[58] Field of Search .................... 549/510, 511; 514/449

[56] References Cited

U.S. PATENT DOCUMENTS 5,322,779  6/1994  Strobel et al. .................... 435/123
5,407,674  4/1995  Gabetta et al. .................... 424/195.1

FOREIGN PATENT DOCUMENTS

WO 95/04154  2/1995  WIPO.

OTHER PUBLICATIONS

Kingston, "The Chemistry of Taxol", Pharmac. Ther., vol. 52, pp. 1–34, 1991.

*Primary Examiner*—Ba K. Trinh
*Attorney, Agent, or Firm*—Woodard, Emhardt, Naughton, Moriarty & McNett

[57] ABSTRACT

A biotransformation process for the production of hydroxylated derivatives of taxol and new derivatives of taxol and cephalomannine are described. A method for converting taxol to L-760,006 and L-760,007, and a method for converting cephalomanine to L-745,596 are provided.

10 Claims, No Drawings

MICROBIAL TRANSFORMATION OF TAXOL AND CEPHALOMANNINE

This application claims the priority of the provisional application Ser. No. 60/006,241 dated Nov. 3, 1995.

BACKGROUND OF THE INVENTION

Taxol is a naturally occurring diterpenoid which has great potential as an anti-cancer drug, and which has shown activity in several tumor systems. Taxol was first isolated and its structure reported by Wani, et al., in "Plant Anti-Tumor Agents. VI. The Isolation And Structure Of Taxol, A Novel Anti-Leukemic And Anti-Tumor Agent From *Taxus brevifolia*," *J. Am. Chem. Soc.*, 1971, 93, 2325. Taxol is found in the stem bark of the Western Yew, *Taxus brevifolia*, as well as in *T. baccata* and *T. cuspidata*.

The biological activity of taxol is related to its effect on cell division. Taxol promotes formation of microtubules that form the mitotic spindle during cell division. Taxol can therefore interfere with depolymerization of the tubulin forming the microtubules of the mitotic spindle, which is essential for cell division to take place. Thus, taxol causes cell division to stop. The mechanism of action of taxol is unique since it promotes the formation of tubulin polymers, whereas other anti-cancer drugs, such as vinblastine and vineristine, prevent microtubule formation.

Extensive testing of taxol was initially delayed because taxol was in short supply. Studies by McGuire et al., found taxol to be an active agent against drug-refractory ovarian cancer. See "Taxol: A Unique Antineoplastic Agent With Significant Activity In Advanced Ovarian Epithelial Neoplasms," *Ann. Int. Med,* 1989, 111, 273–279, herein incorporated by reference. However, due to the low water solubility of taxol, doses had to be delivered as infusions diluted in aqueous dextrose solutions.

It should be noted that in phase 1 clinical trials, taxol itself did not show excessive toxic effects, but severe allergic reactions were caused by the emulsifiers administered in conjunction with taxol to compensate for taxol's low water solubility. In fact, at least one patient's death was caused by an allergic reaction induced by the emulsifiers. Therefore, researchers have attempted to create water soluble derivatives of taxol which retain their anti-neoplastic and anti-cancer activity.

It would be useful to prepare derivatives of taxol. One method of preparing derivatives comprises a bioconversion process. The bioconversion process employs *Streptomyces sp.* MA 7065. In this bioconversion process the taxol and cephalomannine substrates are hydroxylated to yield two principal products. Hydroxylation on the methyl of the 10-acetyl group produces compound L-760,007 in 60% yield. Hydroxylation on the para position of the C-3 benzoamide groups produces compound L-760,006 in 10% yield. The product compounds gave $IC_{50}$ of 7.5 ng/mL in the FAT tubulin polymerization assay compared to 17 ng/mL for taxol. Hydroxylation of the β-methyl group of the tiglamide group produces compound L-745,596.

SUMMARY OF THE INVENTION

A biotransformation process for the production of derivatives of taxol and cephalomannine and novel derivatives of taxol are provided. A method for converting taxol to L-760,006 and L-760,007, and a method for converting cephalomanine to L-745,596 are provided.

DETAILED DESCRIPTION OF THE INVENTION

A biotransformation process for the production of derivatives of taxol and cephalomannine and novel derivatives of taxol are provided. A method for converting taxol to L-760,006 and L-760,007, and a method for converting cephalomanine to L-745,596 are provided.

The present invention is directed to a fermentation process which employs a readily prepared culture medium. Culture medium as used herein is defined as a mixture which supports the growth of microbial cells, which mixture contains ingredients such as peptone, soy peptone, and yeast extract powder. It should be understood that the precise amounts of ingredients provided above may be optimized, or modified so long as no new components are introduced. The key aspect of the medium is its ability to support growth of *Streptomyces sp.* MA 7065 (ATCC 55604) and thereby the production of L-760,006 and L-760,007 useful for pharmaceutical production.

The present invention process can be practiced with any strain of *Streptomyces sp.* capable of producing compounds L-760,006 L-760,007 and L-745,596 and particularly preferred is the *Streptomyces sp.* MA 7065 strain.

In general, the product compounds may be produced by culturing (fermenting) the above-described microorganism in the presence of an appropriate concentration of taxol substrate in an aqueous nutrient medium containing sources of assimilable carbon and nitrogen, preferably under submerged aerobic conditions (e.g., shaking culture, submerged culture, etc.). An appropriate concentration of the parent compound in the aqueous medium ranges from 0.01 mg/ml to 0.5 mg/ml, preferably 0.05 mg/ml. The aqueous medium is incubated at a temperature between 26° C. and 29° C., preferably 27° C. The aqueous medium is incubated for a period of time necessary to achieve the oxidative biotransformation as monitored by HPLC, usually for a period of about 24–48 hours, on a rotary shaker operating at about 220 rpm with a throw of about 2 in. The aqueous medium is maintained at a pH between 6 and 8, preferably about 7, at the initiation and termination (harvest) of the fermentation process. A higher or lower pH will cause the culture to die. A higher pH also leads to a substantial and/or total loss of product. The desired pH may be maintained by the use of a buffer such as morpholinoethanesulfonic acid (MES), morpholinopropane-sulfonic acid (MOPS), and the like, or by choice of nutrient materials which inherently possess buffering properties, such as production media described herein below.

The preferred sources of carbon in the nutrient medium are certain carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form because less pure materials which contain traces of growth factors and considerable quantities of mineral nutrients are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

Submerged aerobic cultural conditions may be preferred for the production of product compounds in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the product compounds.

Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of product compounds and is generally autoclaved to sterilize the medium prior to inoculation. The fermentation medium is generally adjusted to a pH between 6 and 8, preferably about 7, prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°–35° C., for a period of about 10 hours to 20 hours, which may be varied according to fermentation conditions and scales. Preferably, the production cultures are incubated for about 17 hours at 27° C. on a rotary shaker operating at 220 rpm, wherein the pH of the fermentation medium is maintained at 7.0 to harvest.

Preferred culturing/production media for carrying out the fermentation include the following media:

| KE Seed Medium | g/L |
|---|---|
| Glucose | 1.0 |
| Dextrin | 10.0 |
| Beef Extract | 3.0 |
| Ardamine PH | 5.0 |
| NZ Amine Type E | 5.0 |
| $MgSO_4 \cdot 7H_2O$ | 0.05 |
| $K_2HPO_4$ | 0.37 |
| Adjust pH to 7.1 | |
| Add $CaCO_3$ | 0.5 |
| Soy-Glucose Medium | |
| Glucose | 20.0 |
| Soya Meal | 5.0 |
| Yeast Autolysate | 5.0 |
| NaCl | 5.0 |
| Adjust pH to 7.0 | |

The biotransformation products may be recovered from the culture medium by conventional means which are commonly used for the recovery of other known biologically active substances. The product compounds are found in the cultured mycelium and filtrate, which are obtained by filtering or centrifuging the cultured broth, and accordingly can be isolated and purified from the mycelium and the filtrate by a conventional method such as concentration under reduced pressure, lyophilization, extraction with a conventional solvent, such as methanol and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like. A preferred recovery method is solvent extraction, particularly using ethyl acetate. A preferred purification method involves the use of chromatography, especially HPLC, using a reverse-phase silica gel column and an eluant mixture composed of water and organic solvents such as methanol, acetonitrile and the like.

A preferred eluant is composed of water and acetonitrile and is run through the column in a linear gradient. The compound obtained according to the fermentation processes as explained above can be isolated and purified in a conventional manner, for example, extraction, precipitation, fractional crystallization, recrystallization, chromatography, and the like.

This invention further relates to pharmaceutical compositions comprising a therapeutically effective amount of the product compounds in combination with a pharmaceutically acceptable nontoxic carrier or excipient.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, cornstarch and the like a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring.

When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating compounds, sucrose as a sweetening agent and certain preservatives, dyes, coloring and flavors. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

The parenteral preparation can be enclosed in disposable syringes or multiple dose vials made of glass or plastic.

Dosage levels of the compound of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compound of the present invention may be administered on an intermittent basis; i.e., at daily, semi-weekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient.

For external administration the product compounds of Formula I may be formulated within the range of, for example, 0.0001% to 60% by weight, preferably from 0.001 to 10% by weight, and most preferably from about 0.005 to 0.8% by weight. It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

In addition, this invention relates to a method for the treatment of and the prevention of certain afflictions, diseases and illnesses. These compounds are useful as pharmaceutical agents for mammals, especially for humans. These compounds may be administered to patients for use in the treatment of cancer. Examples of the type of cancer which may be treated with the compounds of this invention include, but are not limited to, ovarian, breast and lung cancers.

The present invention also encompasses a method of the treatment of cancer, comprising the administration of a pharmaceutical composition comprising a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

The substrate of the present invention has the following structure:

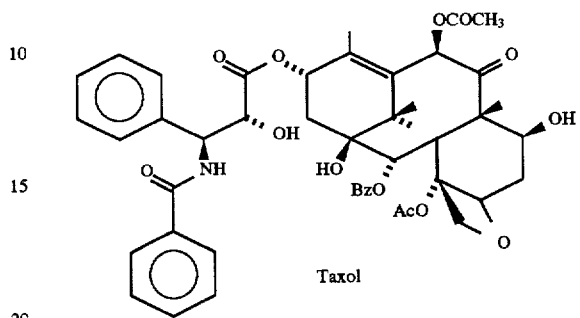

Taxol

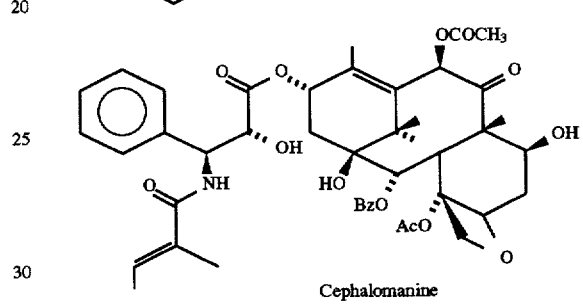

Cephalomanine

The products of the present invention have the following structures:

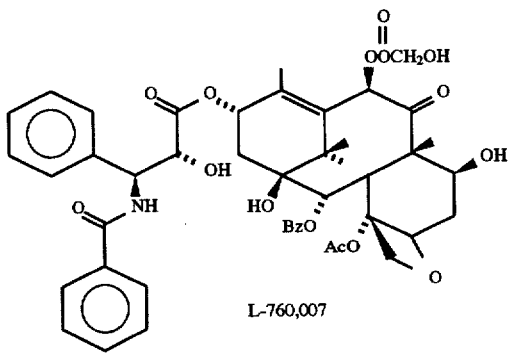

L-760,007

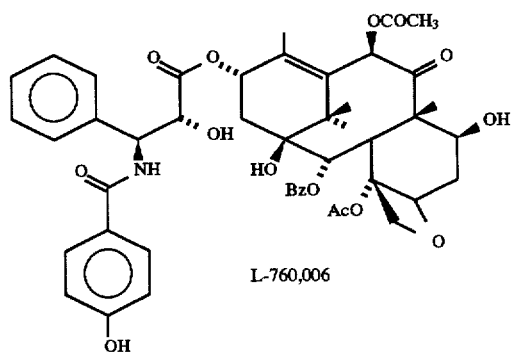

L-760,006

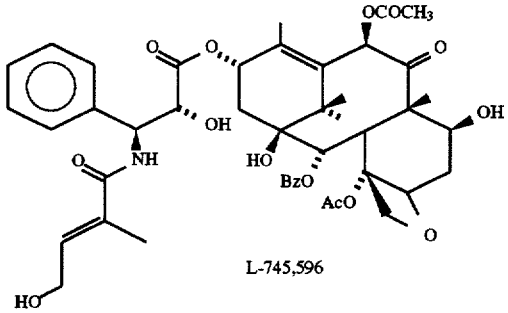

L-745,596

The compounds of the present invention are prepared by fermentation of the microorganism *Streptomyces sp.* MA 7065 (ATCC No. 55604) in the presence of the taxol or cephalomannine substrate under submerged aerobic conditions at an appropriate temperature in an aqueous carbohydrate medium comprising assimilable sources of nitrogen and carbon and isolation of the resulting biotransformation products in a conventional manner. The fermentation is conducted at a pH of about 7 for a sufficient time to selectively hydroxylate the taxol.

A sample of *Streptomyces sp.* MA 7065 was deposited under the Budapest Treaty in the American Type Culture Collection, 12301 Parklawn Drive, Rockville, Md. 20852, USA on Jan. 28, 1993 and has been assigned accession number (ATCC 55604).

The following examples demonstrate the use of *Streptomyces sp.* MA 7065 in the bioconversion of taxol to L-760,006 and L-760,007, and the bioconversion of cephalomannine to L-745,596. The examples are not to be construed as a limitation on the scope of the invention.

EXAMPLE 1
Shake flask fermentations

A frozen vial of *Streptomyces sp.* MA 7065 was used to inoculate a 250 mL baffled shake flask containing 50 mL of KE medium. The seed flask was incubated on a rotary shaker (220 rpm) at 27° C. for 24 hours. An aliquot (2.5 mL) of the seed was used to inoculate a 250 mL non-baffled flask containing 50 mL of Soy-glucose medium. Taxol in DMSO was added to the medium at 0 hr to a final concentration of 0.05 mg/mL. The culture was incubated in the dark at 27° C. on a rotary shaker (220 rpm) for 72 hr.

EXAMPLE 2
Isolation and purification

The fermentation broth of Example 1 was extracted three times with ethyl acetate (3×300 mL). The ethyl acetate residues were combined, dried over sodium sulfate and concentrated under vacuum to an oily residue. The residue was dissolved in acetonitrile and subjected to HPLC. HPLC was performed on an Alltech Econosphere C-18 column (250×10.0 mm) at room temperature and monitored at 235 nm. The column was developed at 3 mL/min with a linear gradient from 37% to 60% acetonitrile in water over 50 min. L-760,006 and L-760,007 were collected during repeated injections of the above described extract. Fractions of retention times 38 and 40 min were pooled and evaporated to yield 1 mg of L-760,006 and 12 mg of L-760,007.

EXAMPLE 3
Characterization

Positive ion FAB-MS gave signals [M+H]+ at m/z 870 and [M+Na]+ at m/z 892 for both derivatives, suggested that they are hydroxylated derivatives. L-760,006 was determined to be the hydroxylation derivative at para position of C-3' benzoamide moiety at phenyl isoserine side chain based on complete assignment of aromatic proton signals by 1D and 2D NMR. L-760,007 was identified as 10- hydroxyacetyl taxol by $^1$H and $^{13}$C analyses. Key features are the absence of methyl proton signal at 2.24 ppm and methyl carbon signal at 20.8 ppm of 10-acetyl group; the presence of novel $CH_2O$ proton signals at 4.17 and 4.29 ppm with large geminal coupling of 17.4 Hz and a new carbon signal at 60.5 ppm; and the presence of carbon signal at 203.2 ppm indicates that C-9 carbonyl group is intact.

EXAMPLE 4

The structures of taxol, L-760,007 and L-760,006 are shown below:

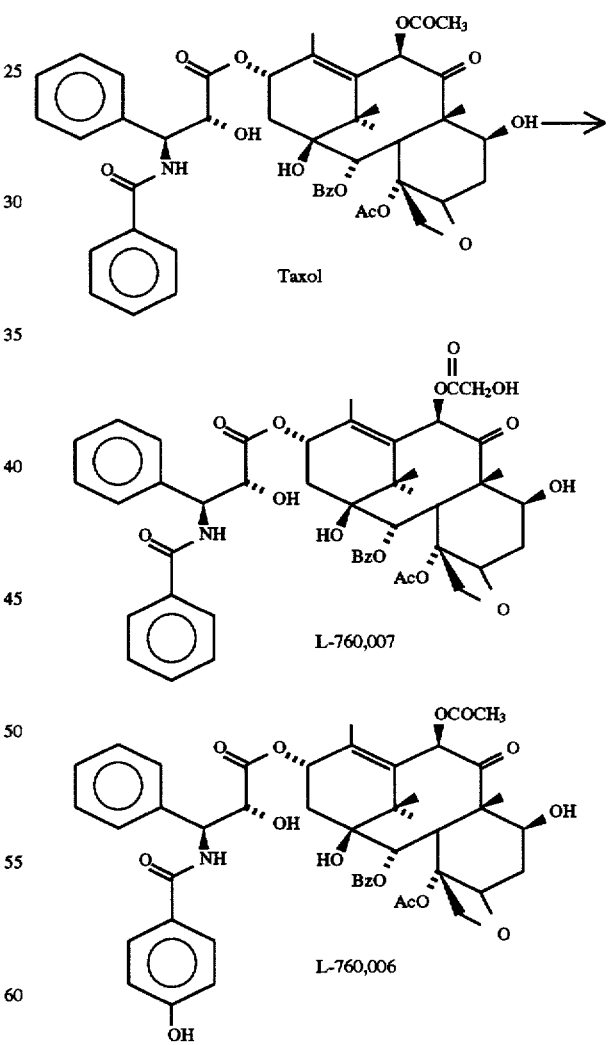

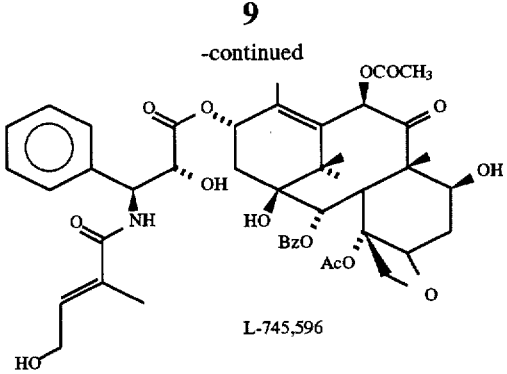

L-745,596

EXAMPLE 5
Preparation of Pharmaceutical Compositions

Salts of L-760,007 and L-760,006 are prepared by methods known to those of skill in the art. The compounds and their salt derivatives are readily formulated into pharmaceutical compositions. The pharmaceutical compositions are useful in the treatment of cancer.

EXAMPLE 6
Method of Treatment

A patient in need of treatment is treated with the pharmaceutical composition of Example 5.

EXAMPLE 7
In Vitro Antitumor Activity

The in vitro antitumor activity cytotoxicity was measured by a microculture assay using 3-(4,5-dimethylthiazol-2-yl)-2,5-diphenyl-tetrazolium bromide (MTT). This assay has an advantage over in vivo assay in that results are obtained within a week as opposed to several months. The assay was done in 96-well microtiter plates. The MTT assay is based on the transformation into a dark blue formazan product by dehydrogenase in the mitochondria of live tumor cells after exposure to drug for 6 days [M. C. Alley, D. A. Scudiero, A. Monks, M. L. Hursey, M. J. Czerwinski, D. L. Fine, B. J. Abbott, J. G. Mayo, R. H. Shoemaker and M. R. Boyd, Cancer Res., 48, 589, 1988.] Thus, only live cells are stained and can be measured at 570 nm. Antitumor cytotoxicity is reported as $GI_{50}$, effect drug dose at which cell growth is retarded to 50% of control culture of tumor cells. The active compounds must have $GI_{50}$ values that are less then $10^{-4}$M or 10 µg/ml.

TABLE

Antitumor Cytotoxicity of Taxanes Against Human Tumor Cell Lines

| Compound | $GI_{50}$ (µg/ml) | | |
|---|---|---|---|
| | A-549 | MCF-7 | HT-29 |
| Taxol | $4 \times 10^{-7}$ | $2 \times 10^{-6}$ | $1 \times 10^{-7}$ |
| Caphalomannine | $1 \times 10^{-4}$ | $8 \times 10^{-4}$ | $2 \times 10^{-4}$ |
| L-760,006 | $4 \times 10^{-5}$ | $1 \times 10^{-5}$ | $8 \times 10^{-5}$ |
| L-760,007 | $<10^{-5}$ | $4 \times 10^{-5}$ | $1 \times 10^{-5}$ |
| L-745,596 | $3 \times 10^{-2}$ | $5 \times 10^{-2}$ | $2 \times 10^{-2}$ |

A-549: lung carcinoma
MCF-7: breast adenocarcinoma
HT-29: colon adenocarcinoma

What is claimed:

1. A method of converting taxol to L-760,006 and L-760,007 which comprises:

(a) cultivating a microorganism in a medium containing taxol; and (b) recovering the L-760,006 and L-760,007.

2. The method of claim 1 wherein the microorganism is *Streptomyces sp.* MA 7065 (ATCC 55604).

3. A compound selected from the group consisting of L-760,006 and L-760,007.

4. A pharmaceutical composition comprising a compound of claim 3.

5. A method of treating a patient having cancer comprising administration of a compound of claim 3 to the patient.

6. A method of converting cephalomanine to L-745,596, which comprises:

(a) cultivating a microorganism in a medium containing cephalomanine; and (b) recovering the L-745,596.

7. The method of claim 1 wherein the microorganism is *Streptomyces sp.* MA 7065 (ATCC 55604).

8. Compound L-745,596.

9. A pharmaceutical composition comprising compound L-745,596.

10. A method of treating a patient having cancer comprising administration of L-745,596 to the patient.

* * * * *